US008426488B2

(12) United States Patent
Ori et al.

(10) Patent No.: US 8,426,488 B2
(45) Date of Patent: Apr. 23, 2013

(54) EASILY REMOVABLE DENTAL CURABLE COMPOSITION

(75) Inventors: Tatsuya Ori, Moriyama (JP); Akari Yamamoto, Moriyama (JP); Masami Arata, Moriyama (JP); Maho Yoshikawa, Moriyama (JP)

(73) Assignee: Sun Medical Co., Ltd., Moriyama-shi (JP)

( * ) Notice: Subject to any disclaimer, the term of this patent is extended or adjusted under 35 U.S.C. 154(b) by 45 days.

(21) Appl. No.: 12/989,357

(22) PCT Filed: Apr. 24, 2009

(86) PCT No.: PCT/JP2009/058595
§ 371 (c)(1),
(2), (4) Date: Dec. 3, 2010

(87) PCT Pub. No.: WO2009/131250
PCT Pub. Date: Oct. 29, 2009

(65) Prior Publication Data
US 2011/0070563 A1    Mar. 24, 2011

(30) Foreign Application Priority Data

Apr. 25, 2008   (JP) .................................. 2008-116160

(51) Int. Cl.
*A61K 6/083*   (2006.01)
(52) U.S. Cl.
USPC ........... 523/105; 523/115; 523/116; 523/117; 523/118; 523/136
(58) Field of Classification Search .......... 523/115–118, 523/105; 526/136
See application file for complete search history.

(56) References Cited

U.S. PATENT DOCUMENTS

| | | | | |
|---|---|---|---|---|
| 4,259,075 | A * | 3/1981 | Yamauchi et al. | 433/217.1 |
| 4,920,188 | A * | 4/1990 | Sakashita et al. | 526/196 |
| 4,985,516 | A * | 1/1991 | Sakashita et al. | 526/196 |
| 5,296,513 | A * | 3/1994 | Ige et al. | 523/115 |
| 6,353,041 | B1 * | 3/2002 | Qian | 523/116 |
| 6,660,784 | B2 * | 12/2003 | Ibaragi et al. | 523/115 |
| 7,090,721 | B2 * | 8/2006 | Craig et al. | 106/35 |
| 2002/0051952 | A1 * | 5/2002 | Kamohara et al. | 433/228.1 |
| 2005/0282116 | A1 | 12/2005 | Kusano | |
| 2009/0258966 | A1 * | 10/2009 | Hirayama et al. | 523/118 |

FOREIGN PATENT DOCUMENTS

| | | |
|---|---|---|
| EP | 923924 A2 * | 6/1999 |
| JP | 49-5143 A | 1/1974 |
| JP | 52-113089 A | 9/1977 |
| JP | 59-15468 A | 1/1984 |
| JP | 6-56618 A | 3/1994 |
| JP | 11-262494 A | 9/1999 |
| JP | 2000-143432 A | 5/2000 |
| JP | 2002-80318 A | 3/2002 |
| JP | 2002-187907 A | 7/2002 |
| JP | 2003-96122 A | 4/2003 |
| JP | 2003-512403 T | 4/2003 |
| JP | 2003-513403 T | 4/2003 |
| JP | 2005-314326 A | 11/2005 |
| JP | 2006-1910 A | 1/2006 |
| JP | 2008-24668 A | 2/2008 |
| WO | WO 98/16187 A1 | 4/1998 |
| WO | WO 9816187 A1 * | 4/1998 |
| WO | WO 01/30302 A1 | 5/2001 |

OTHER PUBLICATIONS

Machine Translation of WO 9816187 A1 (JP98/016187 A1) 1998.*
Hemmi Hiroshi et al.; Tissue Compatibility of Newly-developed Resin Root Canal Sealers; The magazine of the Japanese Society of Conservative Dentistry; vol. 46; No. 5; pp. 690-706; 2003.
Louis I. Grossman et al.; Endodontic Practice; 10th edition; Lea & Febiger, Philadelphia: pp. 296-302; 1981.
English translation of International Preliminary Report on Patentability dated Dec. 23, 2010 for PCT/JP2009/058595 (PCT/IB/338 and PCT/IPEA/409).
International Search Report, PCT/JP2009/058595, Jun. 9, 2009.

* cited by examiner

*Primary Examiner* — James J Seidleck
*Assistant Examiner* — Peter A Salamon
(74) *Attorney, Agent, or Firm* — Birch, Stewart, Kolasch & Birch, LLP

(57) ABSTRACT

An easily removable dental curable composition which prevents the fall or leakage of a temporary prosthetic appliance or a root canal filling material which is easily removed by bonding and adhering it to tooth, shows such high flowability that its operation is easy, has a long working time and excellent X-ray contrast properties and sealability and can be easily removed as required, and a filling kit. The dental curable composition comprises (A) a polymerizable monomer mixture containing a polymerizable monomer having an acid group in the molecule and (B) a polymerization initiator, wherein the component (A) contains (A') a long-chain polymerizable monomer having a structure with a chain length of 17 or more atoms and/or the composition further comprises (D1) a soft resin material.

24 Claims, No Drawings

EASILY REMOVABLE DENTAL CURABLE COMPOSITION

TECHNICAL FIELD

The present invention relates to a curable composition which is temporary or can be removed and can be used for a treatment and to a curable composition suitable for use as a root canal filling material which is applied to the inside of the root canal of a tooth. More specifically, it relates to a temporary filling prosthetic appliance such as a temporary sealing material or temporary cement material which is used temporarily until the final prosthetic appliance is produced or a root canal filling material such as a glue material or sealer used for the treatment of a root canal. In the case of the root canal filling material, the present invention relates to an easily removable dental curable composition which is excellent in root canal filling properties, adhesion to tooth and root canal sealability and has X-ray contrast properties for the confirmation of a filled state and the excellent removability of a cured root canal filling curable composition if retreatment of root canal is needed.

BACKGROUND ART

There is a case where the dental treatment must proceed to the next step after the confirmation of the sedation and treatment effect of a morbid part. In this case, a dental material is used to protect the infected part which has been sedated and temporarily compensate for a lost part. This dental material must be removed after a certain period of time. Therefore, the dental material needs to have such properties as ease of removal. In a prosthetic treatment, the production of a prosthetic appliance such as an inlay or crown which is produced outside the oral cavity takes at least a few days. Therefore, a dental composition (to be referred to as "temporary prosthetic appliance" hereinafter) as a substitute for a drilled tooth must adhere to tooth and must be held in a cavity formed by removing dental caries or a lost part for a certain period of time. Further, ease of removal is also required as the temporary prosthetic appliance must be removed after the completion of the prosthetic appliance. Since tooth and the temporary prosthetic appliance have been held simply by mechanical retention force, there are many problems to be solved, such as the occurrence of separation between them by a temperature change in the oral cavity or by occlusal force when food is chewed in, the breeding of bacteria due to the formation of a space, or the onset of pain.

Before the dental treatment of a dental pulp disease or an apical periodontal disease is carried out, a root canal treatment for cutting off the infection route between the root canal and the periodontal tissue or between the root canal and the oral cavity is widely carried out by filling a pulp cavity or a root canal formed when a nerve (dental pulp) is removed with a stable substance to close the space. To carry out the root canal treatment again when the initially treated part is infected unfortunately, a temporary sealing material is used to temporarily cut off the root canal infected part in the jawbone from the outside world until it is sedated. Even for the root canal treatment after sedation, there is known a method in which a root canal is filled with root filler gutta-percha filling material which is a rubber-like composition comprising natural resin gutta-percha and zinc oxide as the main ingredients together with a cement and a sealer to be mechanically stuffed and sealed. It is desired that this root filling material and the sealer should be removable for the recurrence of an infected part.

Details of the required conditions for the ideal root canal filling material are suggested by Grossman as described in Grossman, L. I.: Endodontic practice; $10^{th}$ ed., Lea & Febiger, Philadelphia, 296-302, 1981. That is, the ideal root canal filling material has (1) high flowability that it is easily manipulated and ample working time (time during which it can be handled), (2) high dimensional stability, (3) ability to seal a root canal in both lateral and vertical directions, (4) no irritation to periapical tissues, (5) imperviousness to water, (6) insolubility without being corroded, (7) ability to prevent the growth of bacteria, (8) X-ray contrast properties, (9) no change in the color of tooth, (10) abacterial properties and (11) removability.

Most of existing materials are epoxy-based resins, resin-based curable compositions and glass ionomer cements which comprise polyacrylic acid and aluminosilicate glass as the main ingredients and are said to be cured through an acid-base reaction, besides the above-described root filling gutta-percha. Most of them are thermoplastic resins which are provided with X-ray contrast properties by blending an X-ray impermeable filler. These resins are heated to be provided with flowability right before they are applied to be filled into a root canal and cured while they achieve the same temperature as the temperature of the body. Since these resins have no interaction with the root canal wall, they are unsatisfactory in terms of the sealability of the root canal wall and adhesion to the root canal wall. Further, as they do not have adhesion to a sealer and a gutta-percha point, the root canal cannot be bonded and sealed completely clinically.

Lack of sealability and adhesion causes the inclusion of extraneous foreign matter into the dentine of the root canal, and the disintegration of a dental root and a bad influence upon the alveolar bone are conceivable due to the poor hygiene of the inside of the root canal. Further, since adhesion to the root canal wall by means of a thermoplastic resin of the prior art can be almost unexpected, there is possibility that sealability and adhesion may be impaired when mechanical or physical external force is applied to the root canal wall. Meanwhile, there is proposed an adhesion material for bonding enamel or dentine which is rich in calcium component as compared with the inside of the root canal.

Up till now, the following proposals have been made as root canal filing materials.

JP-A 49-5143 proposes a filling material for the treatment of a dental caries which comprises tributyl borane as a polymerization initiator. However, since it is not used as a root canal filling material, its cured product has no X-ray contrast properties and does not comprise a polymerizable monomer containing an acid group which should be interacted with the root canal wall.

Although JP-A 52-113089 discloses an aluminum oxide filler as a dental material, it is not used as a root canal filling material and therefore high X-ray contrast properties cannot be provided to this filler.

JP-A 59-15468 has a description of various fillers which do not show satisfactory X-ray contrast properties. X-ray contrast properties can be provided to the filler described in the above proposal when it is used in a composition but a root canal cannot be filled with it as its flowability degrades. The adhesive material of the proposal comprises a component which can interact with the surface of tooth. However, as it is not used to fill a root canal, its operation time is extremely short or it has no X-ray contrast properties or no sufficiently high sealability.

WO98/16187 proposes a root canal filling composition which comprises a thixotropy providing agent for adjusting viscosity and flowability and an X-ray impermeable filler as well as a pre-treatment material suitable for use in the composition. Although the proposed material has excellent manipulation ease and performance as a root canal filling material, when the thixotropy providing agent and the X-ray impermeable filler are kept in a mixed state, there is a case where target manipulation ease is not obtained due to separation or settling caused by the difference in specific gravity between them.

JP-A 2005-314326 proposes a root canal filling curable composition which comprises two different types of X-ray impermeable fillers which are fine particles having a particle diameter of 0.001 to 1 µm and particles having a particle diameter of 2 to 50 µm, can adjust viscosity and flowability by their weight ratio without containing a thixotropy providing agent for adjusting viscosity and flowability and has excellent dentine adhesion and root canal sealability. However, there is a case where it is difficult to remove the cured root canal filling curable composition when retreatment of root canal is needed.

A root canal filling composition comprising two different types of zirconium oxides which differ in particle diameter is suggested in the magazine of the Japanese Society of Conservative Dentistry, vol. 46, No. 5, pp. 690-706, 2003 as a composition described in WO98/16187. However, when the composition is kept for a long time, there is a case where target manipulation ease is not obtained due to separation or settling.

DISCLOSURE OF THE INVENTION

It is an object of the present invention which has been made to solve the above problems to provide an easily removable dental curable composition which prevents the fall or leakage of a temporary prosthetic appliance or a root canal filling material which is easily removed by bonding and adhering it to dentine, shows such high flowability that its operation is easy, has a long working time and excellent X-ray contrast properties and sealability and can be easily removed as required.

It is another object of the present invention to provide a composition having excellent storage stability and a filling kit which is a combination of the easily removable dental curable composition of the present invention and a tooth surface treating agent suitable for use with the composition.

Other objects and advantages of the present invention will become apparent from the following description.

According to the present invention, firstly, the above objects and advantages of the present invention are attained by a dental curable composition comprising (A) a polymerizable monomer mixture containing a polymerizable monomer having acid group(s) in the molecule and (B) a polymerization initiator, wherein the component (A) contains (A') a long-chain polymerizable monomer having a structure with a chain length of 17 or more atoms and/or the composition further comprises (D1) a soft resin material; and when the amount of the component (A') based on 100 parts by weight of the component (A) is represented by [a'] and the amounts of the components (A), (B) and (D1) based on 100 parts by weight of the total of the components (A) and (B) are represented by (a), (b) and (d1), respectively, the following expressions (1) to (5) are satisfied:

$$70 \leq (a) \leq 99.99 \quad (1)$$

$$0.01 \leq (b) \leq 30 \quad (2)$$

$$1 \leq [a']/5 + (d1)/1 \quad (3)$$

$$[a'] \leq 95 \quad (4)$$

$$(d1) \leq 250 \quad (5).$$

According to the present invention, secondly, the above objects and advantages of the present invention are attained by an easily removable dental curable composition comprising ($A_1$) a monofunctional polymerizable monomer mixture containing 0.1 to 30 wt % of a monofunctional polymerizable monomer having acid group(s) in the molecule and 99.9 to 70 wt % of a monofunctional polymerizable monomer having no acid group in the molecule, (B) a polymerization initiator, (C) an X-ray impermeable filler and (D1) a soft resin material, wherein the amount of the component ($A_1$) is 1 to 70 parts by weight, the amount of the component (B) is 0.1 to 20 parts by weight, the amount of the component (C) is 1 to 80 parts by weight and the amount of the component (D1) is 0.1 to 60 parts by weight based on 100 parts by weight of the total of the components ($A_1$), (B), (C) and (D1).

According to the present invention, thirdly, the above objects and advantages of the present invention are attained by a dental kit which is a combination of the easily removable dental curable composition of the present invention and a tooth surface treating agent.

The above component (B) is a polymerization initiator, preferably a boron-containing polymerization initiator.

The above component (C) is preferably at least one selected from the group consisting of zirconium oxide, zinc oxide, barium sulfate, bismuth oxide, bismuth oxychloride, bismuth oxide carbonate and calcium tungstate.

The above soft resin material (D1) is preferably a resin which is not substantially dissolved by the component (A) or ($A_1$), more preferably at least one selected from the group consisting of gutta-percha, polyethylene, polypropylene, ethylene propylene copolymer, ethylene propylene terpolymer, polyisoprene, ethylene vinyl acetate copolymer, silicone polymer and acrylate copolymer. The resin preferably has a durometer A hardness of not more than 90 or a durometer D hardness of not more than 60.

The above gutta-percha comprises polyisoprene which is a natural rubber or a rubber-like substance (natural or synthetic polymer) comprising polyisoprene as the main ingredient, additives and an inorganic compound (for example, zinc oxide, barium sulfate or heavy metal salt) X-ray contrast agent or an organic compound such as a wax and is known per se and available in various forms. In the present invention, the terms "gutta-percha point", "gutta-percha corn" and "gutta-percha chip" mean a needle-like cured product comprising gutta-percha, a small-sized candle-like cylindrical cured product and a particulate cured product larger than a powder in size, respectively. Meanwhile, as synthetic polyisoprene, cis-polyisoprene, trans-polyisoprene and atactic polyisoprene which is a mixture thereof may be used. Out of these, trans-polyisoprene is preferably used. The above natural and synthetic polymers may be used alone or in combination as the component (A) or ($A_1$).

The curable composition of the present invention may further comprise the following components (D2), (E), (F), (G) and (H).

The component (D2) is a polymer except for the component (D1), which is swollen or dissolved by the component (A) (or $A_1$)). When the component (D2) is contained, the amount of the component (D2) is preferably 0.1 to 60 parts by weight based on 100 parts by weight of the total of the component (A) (or ($A_1$)), (B), (C) and (D1) (when the component (A) is used, the total amount of the component (C) and/or the component (D) can be 0. The same shall apply to the other components (E) to (H)).

The component (E) is a polyfunctional polymerizable monomer. When the component (E) is contained, the amount of the component (E) is preferably 0.05 to 20 parts by weight based on 100 parts by weight of the total of the components ($A_1$), (B), (C) and (D1).

The component (F) is a disinfecting agent. When the component (F) is contained, the amount of the component (F) is preferably 0.01 to 20 parts by weight based on 100 parts by weight of the total of the components (A) (or ($A_1$)), (B), (C) and (D1).

The above component (F) is preferably at least one selected from the group consisting of benzalkonium chloride, benzethonium chloride, isopropyl methyl phenol, cetyl pyridinium chloride, resorcin, chlorhexidine hydrochlorate, chlorhexidine gluconate, iodine, potassium iodide, povidone-iodine and iodoform.

The component (G) is a solvent. When the component (G) is contained, the amount of the component (G) is preferably 0.1 to 100 parts by weight, more preferably 0.3 to 50 parts by weight, much more preferably 0.5 to 25 parts by weight based on 100 parts by weight of the total of the components (A) or ($A_1$), (B), (C) and (D1).

The component (H) is a filler. When the component (H) is contained, the amount of the component (H) is preferably 0.1 to 30 parts by weight based on 100 parts by weight of the total of the components (A) (or ($A_1$)), (B), (C) and (D1).

The above component (H) is preferably at least one selected from the group consisting of an inorganic filler and an organic composite filler.

BEST MODE FOR CARRYING OUT THE INVENTION

The easily removable dental curable composition of the present invention and the above components will be described hereinunder.

The dental curable composition of the present invention is a dental composition which comprises (A) a polymerizable monomer and (B) a polymerization initiator, wherein the component (A) contains (A') a long-chain polymerizable monomer having a structure with a chain length of 17 or more atoms and/or the composition comprises (D1) a soft resin material; and when the amount of the component (A') contained in the component (A) based on 100 parts by weight of the component (A) is represented by [a'] and the amounts of the components (A), (B) and (D1) based on 100 parts by weight of the total of the component (A) which may contain the component (A') and the component (B) are represented by (a), (b) and (d1), respectively, the following expressions (1) to (5) are satisfied:

$$70 \leq (a) \leq 99.99 \tag{1}$$

$$0.01 \leq (b) \leq 30 \tag{2}$$

$$1 \leq [a']/5 + (d1)/1 \tag{3}$$

$$[a'] \leq 95 \tag{4}$$

$$(d1) \leq 250 \tag{5}$$

The dental curable composition of the present invention comprises (A) a polymerizable monomer. The polymerizable monomer is not particularly limited as long as it is a monomer which is polymerized by a radical polymerization initiator, and a monomer having a (meth)acryloyl group, styryl group, vinyl group or allyl group as a polymerizable group is used.

In this text, "(meth)acrylate" is a generic term for both acrylate and methacrylate, and the same shall apply to "(meth)acrylic acid" and "(meth)acryloyl group".

The component (A) of the present invention has (A') a long-chain polymerizable monomer having a structure with a chain length of 17 or more atoms (long-chain component) and/or another component (short-chain component), each of these two components has a component having an acid group (acidic component) and/or a component having no acid group (non-acidic component), and further each of these two components may include a component having a plurality of polymerizable groups (polyfunctional component) and a component having only one polymerizable group (monofunctional component).

Further, in the polymerizable monomer (A) of the present invention, for convenience sake, the acidic short-chain polyfunctional component should belong to the acidic short-chain monofunctional component, and the acidic long-chain monofunctional component, the acidic long-chain polyfunctional component and the non-acidic long-chain monofunctional component should belong to the non-acidic long-chain polyfunctional component.

The polymerizable monomer (A) used in the present invention should contain at least one polymerizable group in one molecule.

In the present invention, examples of the polymerizable monomer (A) include monofunctional polymerizable monomers having one polymerizable group in one molecule, bifunctional polymerizable monomers having two polymerizable groups in one molecule and polyfunctional polymerizable monomers having 3 or more polymerizable groups in one molecule (for example, polyfunctional (meth)acrylic acid esters), all of which are suitably selected according to use purpose.

Out of the polymerizable monomers, long-chain polymerizable monomer (A') having a structure with a chain length of 17 or more atoms (preferably 19 to 300 atoms, more preferably 25 to 200 atoms, much more preferably 30 to 100 atoms) are preferably used as the component (A) from the viewpoint of enhancing the flexibility and removability of a cured product. As for the structure of the long chain, as long as the component (A') has a sufficiently long molecular chain and flexibility, it is not limited to a specific chemical structure. Polyalkylene glycol di(meth)acrylates having 4 or more oxyalkylene recurring units ($—(—(—CH_2—)_p—O—)_n—$; p is 2 or more, n is 4 or more) are preferably used, and polyethylene glycol di(meth) acrylate and/or polypropylene glycol di(meth) acrylate having preferably 4 to 30, more preferably 7 to 25, much more preferably 9 to 23 recurring units derived from propylene glycol and/or ethylene glycol are/is more preferably used. When the number of atoms or the number of recurring units falls below the lower limit, it is difficult to remove a cured product and when the number exceeds the upper limit, polymerization becomes incomplete disadvantageously.

As for the chain length of the above long-chain polymerizable monomer, it is assumed that the free rotation of a bond between atoms has a great influence upon flexibility. Therefore, a double bond is considered as undesirable. Therefore, for the calculation of the number of atoms, the number of atoms excluding a double bond and so on is preferably used. Stated more specifically, on the route of the target molecular chain, an atom group bonded by a double bond (>C=C<) is counted as one atom. This is because an atom bonded by a single bond has two freely rotatable bond axes on the molecular chain whereas two carbon atoms which are double bonded on the route of the molecular chain have only two free rotatable bond axes in total. An aromatic ring and a condensed ring thereof should be considered and counted also as one atom. A 3- or 4-membered saturated ring may be considered and counted also as one atom. A 5 or more-membered ring has conformational freedom to be changed into a chair-like or boat-like ring but there is limitation. Therefore, ¼ the number of atoms should be added with the result that the total should be 1+¼. Every time a 5 or more-membered ring is added as a condensed ring, ¼ the number of atoms should be added. In accordance with this, in the case of a bicyclo-condensed ring (example; completely hydrogen saturated naphthalene ring), the total number of atoms is 1+¼+¼. In the case of a Spiro ring, the ring should be treated as one saturated ring having a number of atoms obtained by subtracting two atoms without changing the number of atoms on the route as much as possible. When a plurality of routes can be selected like the above rings, the shortest route should be selected. It is not necessary to take into special consideration a double bond which is not existent on the molecular chain like the oxygen of carbonyl. The number of atoms (such as hydrogen atoms) at the ends of the molecular chain is not counted.

Further, the long-chain polymerizable monomer (A') has preferably at least two polymerizable groups, more preferably a polymerizable double bond at both ends of the long-chain structure. Alternatively, it is important that it should have the long-chain structure between at least two polymerizable double bonds. Probably it is considered that the moderately condensed form of the long-chain structure is predominant over the elongated form thereof in stable thermodynamic equilibrium and when the polymerizable double bonds at the both ends form the crosslink of polymer molecules. When the long-chain polymerizable monomer is polymerized and cured to enter the polymerization shrinkage stage, the above condensed form changes into the elongated form, thereby contributing to the alleviation of the stress of polymerization shrinkage. For example, long-chain polymerizable monomers having 4 to 30 recurring units (n) derived from polyethylene glycol or polypropylene glycol and represented by the following formulas (III) and (Iv) are particularly preferably used.

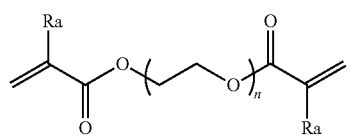
(III)

(in the formula (III), Ra is H or CH$_3$, and n is 4 to 30.)

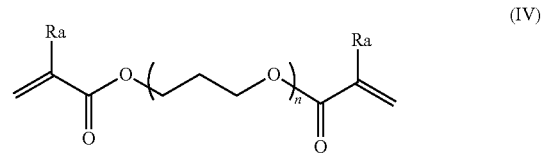
(IV)

(in the formula (IV), Ra is H or CH$_3$, and n is 4 to 30.)

Besides the above monomers, a polymerizable monomer containing a hydroxyl group in the molecule, a polymerizable monomer containing a triazine ring derivative and represented by the following formula (V) (including an isocyanurate (meth)acrylate ester), or a dipentaerythritol-based polymerizable monomer represented by the following formula (VI) is particularly preferably used as the component (A), and they may be used alone or in combination.

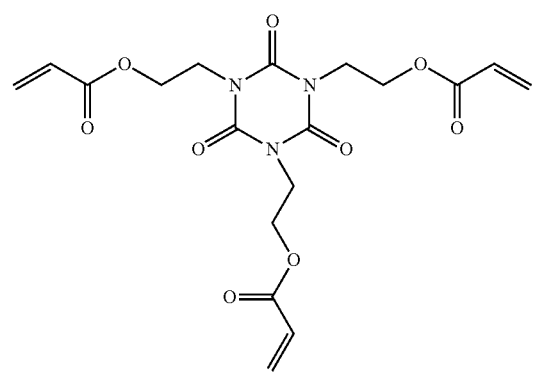
(V)

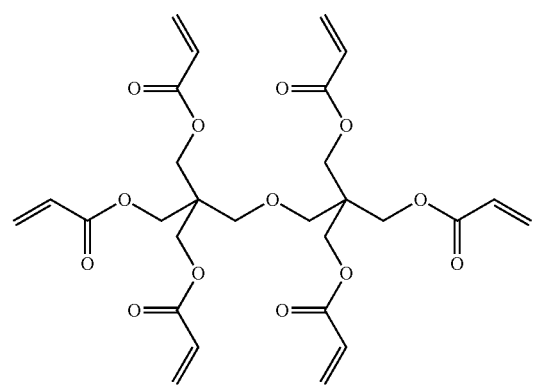
(VI)

The triazine ring derivative which is not particularly limited is, for example, a substitution product obtained by substituting at least one hydrogen atom of a triazine ring by another substituent having a polymerizable functional group, or a derivative obtained by introducing a substituent having a polymerizable functional group into a carbon or nitrogen atom constituting a ring by saturating at least one of the double bonds of a triazine ring. It is preferably a derivative obtained by introducing a substituent having a polymerizable functional group into a nitrogen atom by saturating the double bond of the ring structure of a triazine ring to carbonylate a carbon atom, that is, a compound having a structure represented by the following formula (VII) which is an isocyanurate-based compound. In the formula (VII), $R_{17}$, $R_{18}$ and $R_{19}$ are each independently a polymerizable group, for example, a radically polymerizable unsaturated group having a (meth)acryloyl group, vinyl group or allyl group.

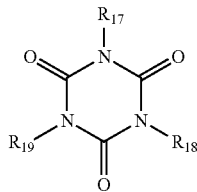

(VII)

These polymerizable monomers may be used alone or in combination.

Although the above polymerizable monomers have no acid group in the molecule, the polymerizable monomer (A) in the present invention includes a polymerizable monomer containing an acid group in the molecule.

The component (A) in the present invention contains preferably 1 to 70 parts by weight, more preferably 5 to 50 parts by weight, much more preferably 10 to 30 parts by weight of a polymerizable polyfunctional (meth)acrylate having 3 or more ethylenically unsaturated bonds (based on 100 parts by weight of the whole component (A)). Below the above lower limit, the mechanical strength of the polymer may become unsatisfactory and above the upper limit, the polymer may become brittle.

The component (A) in the present invention contains preferably 1 to 70 parts by weight, more preferably 10 to 50 parts by weight, much more preferably 20 to 40 parts by weight of a polymerizable monomer having a triazine ring derivative (based on 100 parts by weight of the whole component (A)). Below the above lower limit, the surface hardness of the polymer may become unsatisfactory and above the upper limit, the polymer may become brittle.

The component (A) in the present invention contains preferably 1 to 80 parts by weight, more preferably 10 to 60 parts by weight, much more preferably 20 to 40 parts by weight of a dipentaerythritol-based polymerizable monomer (based on 100 parts by weight of the whole component (A)). Below the above low limit, the surface hardness of the polymer may become unsatisfactory and above the upper limit, the polymer may become brittle.

The component (A) in the present invention may contain a component included in the monofunctional polymerizable monomer mixture ($A_1$) which will be described hereinafter as a matter of course.

[Monofunctional Polymerizable Monomer Mixture ($A_1$)]

The monofunctional polymerizable monomer mixture as the component ($A_1$) in the present invention contains 0.1 to 30 wt % of a polymerizable monomer having an acid group in the molecule and 99.9 to 70 wt % of a monofunctional polymerizable monomer having no acid group in the molecule. It should be understood that the characteristic properties of the monofunctional polymerizable monomer mixture ($A_1$) are also applied to the mixture (A) as long as there is no inconsistency. Examples of the acid group of the monomer include carboxylic acid group, carboxylic anhydride group, phosphoric acid group, pyrophosphoric acid group, sulfonic acid group, thiocarboxylic acid group, thiophosphoric acid group, sulfinic acid group and acid anhydrides thereof. Although it cannot be said that the acid anhydride group such as carboxylic anhydride group is apparently an acid group, it is considered as an acid group because it easily changes into an acid group under a moisture condition at normal temperature. Examples of the polymerizable functional group of the monomer include radically polymerizable unsaturated groups having an acryloyl group, methacryloyl group (both may be collectively referred to as "(meth)acryloyl group" hereinafter), styryl group, vinyl group or allyl group. The monofunctional polymerizable monomer is a polymerizable monomer having one of the above polymerizable groups in one molecule.

Out of the monofunctional polymerizable monomers having an acid group, monofunctional polymerizable monomers having a carboxyl group or a functional group corresponding to this (such as a carboxylic anhydride group) in one molecule include monocarboxylic acids, dicarboxylic acids, tricarboxylic acids, tetracarboxylic acids, polycarboxylic acids and anhydrides thereof. Specific examples of the monofunctional polymerizable monomers include monomers having a carboxyl group directly bonded to a vinyl group such as (meth)acrylic acid, fumaric acid and maleic acid; monomers having an aromatic ring between a vinyl group and a carboxyl group such as p-vinylbenzoic acid; aliphatic carboxylic acids having a (meth)acryloyloxy group and at least one carboxyl group such as 11-(meth) acryloyloxy-1,1-undecanedicarboxylic acid (MAC-10 in the case of methacrylate) and anhydrides thereof; monocyclic aromatic carboxylic acids having a chain hydrocarbon with at least one (meth)acryloyloxy group and at least one carboxyl group such as 4-(meth)acryloyloxymethyltrimellitic acid, 4-(meth)acryloyloxyethyltrimelitic acid (4-MET in the case of methacrylate, 4-META in the case of methacrylate of an anhydride), 4-(meth)acryloyloxybutyltrimellitic acid, 1,4-di(meth)acryloyloxyethylpyromellitic acid and 4-[2-hydroxy-3-(meth)acryloyloxy]butyltrimellitic acid and anhydrides thereof, polycyclic aromatic carboxylic acids having a chain hydrocarbon with at least one (meth) acryloyloxy group and at least one carboxyl group such as 6-(meth) acryloyloxyethylnaphthalene-1,2,6-tricarboxylic acid and anhydrides thereof; monocyclic aromatic carboxylic acids having a chain hydrocarbon with at least one (meth)acryloyloxy group and at least one hydrophilic functional group such as hydroxyl group and at least one carboxyl group such as 4-[2-hydroxy-3-(meth) acryloyloxy]butyltrimellitic acid and anhydrides thereof; (meth)acrylates of an alcohol having at least one benzoyloxy with at least one carboxyl group such as 2,3-bis(3,4-dicarboxybenzoyloxy)propyl(meth)acrylate, benzoic acids having at least one (meth)acryloyloxy such as 2-, 3- or 4-(meth)acryloyloxybenzoic acid; amino acids having an N-(meth)acryloyl group and/or an O-(meth)acryloyloxy group such as O-(meth) acryloyloxy-N-(meth)acryloyltyrosine, O-(meth)acryloyloxytyrosine, N-(meth)acryloyltyrosine and N-(meth)acryloyloxyphenylalanine, N- and/or O-mono- or di(meth)acryloylaminobenzoic acids such as N-(meth)acryloyl-p-aminobenzoic acid, N-(meth) acryloyl-O-aminobenzoic acid, N-(meth)acryloyl-5-aminosalicylic acid (5-MASA in the case of methacrylate) and N-(meth) acryloyl-4-aminosalicylic acid; adduct of N-phenylglycin or N-tolylglycin with glycidyl(meth)acrylate; and aminophthalic acids obtained by bonding a chain hydrocarbon group having a hydrophilic group such as hydroxyl group and a (meth)acryloyloxy group to an amino group and/or a carboxyl group such as 4-[(2-hydroxy-3-(meth)acryloyloxypropyl) amino]phthalic acid and 3- or 4-[N-methyl-N-(2-hydroxy-3-(meth)acryloyloxypropyl)amino]phthalic acid. Out of these, 11-methacryloyloxy-1,1-undecanedicarboxylic acid (MAC-10) and 4-methacryloyloxyethyltrimellitic acid (4-MET) or anhydride thereof (4-META) and 5-MASA are preferably used.

The polymerizable monomers having a phosphoric acid group or thiophosphoric acid group in one molecule include alkylacid phosphates having at least one (meth)acryloyloxy group such as 2-(meth)acryoloyloxyethylacid phosphate and 2- and/or 3-(meth)acryloyloxypropylacid phosphate, 4-(meth)acryloyloxybutylacid phosphate, 6-(meth)acryloyloxyhexylacid phosphate, 8-(meth)acryloyloxyoctylacid phosphate, 10-(meth)acryloyloxydecylacid phosphate and 12-(meth)acryloyloxydodecylacid phosphate; and aromatic acid phosphates having an alkyl group with at least one (meth) acryloyloxy group and 0 or more other substituents such as 2-(meth)acryloyloxyethylphenylacid phosphate and 2-(meth)acryloyloxyethyl-p-methoxyphenylacid phosphate. The phosphoric acid group in these compounds may be substituted by a thiophosphoric acid group. Out of these, 2-(meth)acryloyloxyethylphenylacid phosphate and 10-(meth)acryloyloxydecylacid phosphate are preferably used.

Out of the polymerizable monomers which can be used as the component ($A_1$), the polymerizable monomers having at least one pyrophosphoric acid group in one molecule include di{(meth)acryloyloxyalkyl}pyrophosphate compounds such as di{2-(meth)acryloyloxyethyl}pyrophosphate, di{4-(meth)acryloyloxybutyl}pyrophosphate, di{6-(meth)acryloyloxyhexyl}pyrophosphate, di{8-(meth)acryloyloxyoctyl}pyrophosphate and di{10-(meth)acryloyloxydecyl}pyrophosphate. These polymerizable monomers having a pyrophosphate group(s) may be used alone or in combination.

The polymerizable monomers having a sulfonic acid group in one molecule include alkyl(meth)acrylates having at least one sulfonic acid group and 0 or more other substituents (alkyl, halogen or alkoxy) such as 2-sulfoethyl (meth)acrylate, 2- or 1-sulfo-1 or 2-propyl(meth)acrylate, 1- or 3-sulfo-2-butyl(meth)acrylate 3-bromo-2-sulfo-2-propyl(meth)acrylate and 3-methoxy-1-sulfo-2-propyl (meth)acrylate; and alkyl (meth) acrylamides having at least one sulfonate group and 0 or more other substituents (alkyl, halogen or alkoxy) such as 1,1-dimethyl-2-sulfoethyl (meth)acrylamide. Out of these, 2-methyl-2-(meth) acrylamide propanesulfonic acid is preferably used.

The polyfunctional polymerizable monomer (E) which can be added to the component ($A_1$) may contain an acid group in the molecule. A polyfunctional polymerizable monomer having at least one carboxyl group in one molecule is selected from a monocarboxylic acid, dicarboxylic acid, tricarboxylic acid, tetracarboxylic acid and derivatives thereof. Specific examples of the polyfunctional polymerizable monomer (E) include esters of a hydroxyalkyl (meth)acrylate and a monocyclic aromatic carboxylic acid having at least one carboxyl group such as an adduct (PMDM) of 2-hydroxyethyl (meth) acrylate with pyromellitic dianhydride; esters of a hydroxyalkyl (meth)acrylate and a vinyl-based, benzophenone-based or biphenyl-based carboxylic acid having at least one carboxyl group such as an adduct obtained by reacting 2 moles of 2-hydroxyethyl (meth)acrylate with 1 mole of maleic anhydride, 3,3',4,4-benzophenonetetracarboxylic dianhydride (BTDA) or 3,3',4,4'-biphenyltetracarboxylic dianhydride; and chain hydrocarbons having a benzoyloxy-based substituent with at least one carboxyl group and at least two (meth) acryloyloxy groups such as 2-(3,4-dicarboxybenzoyloxy)-1,3-di(meth) acryloyloxypropane.

As for the polyfunctional polymerizable monomer which is used as the component (E), polyfunctional polymerizable monomers having at least one phosphate group or thiophosphate group in one molecule include alkylacid phosphates having at least two (meth)acryloyloxy groups such as bis{2-(meth)acryloyloxyethyl}acid phosphate and bis{2- or 3-(meth)acryloyloxypropyl}acid phosphate. The phosphate group in these compounds may be substituted by a thiophosphate group.

The monofunctional polymerizable monomer having an acid group in one molecule may have a substituent such as an amino group, amido group, cyano group, nitrile group, hydroxyl group, thiol group or halogen atom in the molecule in addition to the acid group. Part or all of the acid group may form a metal salt or a complex, or may form an ammonium salt or a complex with ammonia. It may form an adduct with another amino compound. These monofunctional polymerizable monomers having an acid group may be used alone or in combination of two or more.

In the present invention, the monofunctional polymerizable monomer having an acid group must be used in an amount of 0.1 to 30 wt %, preferably 0.5 to 25 wt %, more preferably 1 to 20 wt % of the monofunctional polymerizable monomer mixture ($A_1$).

The acid group of the polymerizable monomer having an acid group in the molecule is existent in the component ($A_1$) of the present invention in an amount of preferably 0.00001 to 0.03 mole/g, more preferably 0.0001 to 0.01 mole/g, much more preferably 0.0005 to 0.006 mole/g in terms of a monovalent acid group.

The value in terms of the monovalent acid group is equivalent to the mole/g of a carboxyl group when $1H^+$ is released from an acid-base neutralization reaction like the carboxyl group as the acid group and to 2 times the mole/g of a phosphate group ($-H_2PO_4$) when $2H^+$ is released from an acid-base neutralization reaction like the phosphate group.

Below the above lower limit, the degree of acidity for decalcifying the surface of a tooth may become unsatisfactory and above the upper limit, the surface of a tooth may be decalcified too much.

The hydroxyl group of the polymerizable monomer having an alcoholic hydroxyl group is existent in the component ($A_1$) of the present invention in an amount of preferably 0.00001 to 0.02 mole/g, more preferably 0.0001 to 0.01 mole/g, much more preferably 0.001 to 0.008 mole/g. Below the above lower limit, hydrophobic nature becomes strong, thereby reducing compatibility with water and above the upper limit, the water resistance of the polymer tends to lower.

When the amount of the monomer having an acid group falls within the above range, the conversion of the monofunctional polymerizable monomer mixture ($A_1$) into a polymer can be increased, thereby making it possible to reduce the amount of the residual unpolymerized monomer to preferably not more than 3 wt %, more preferably not more than 1 wt %, most preferably not more than 0.5 wt %.

Examples of the monofunctional polymerizable monomer having no acid group in the molecule include aliphatic esters of (meth)acrylic acid such as methyl (meth)acrylate, ethyl (meth)acrylate, propyl (meth)acrylate, isopropyl (meth)acrylate, butyl (meth)acrylate, pentyl (meth)acrylate, isopentyl (meth)acrylate and hexyl (meth)acrylate; aromatic esters such as phenyl (meth)acrylate; heterocyclic (meth)acrylates containing an oxygen atom and so on such as glycidyl (meth) acrylate and tetrahydrofurfuryl (meth)acrylate; (meth)acrylates containing a hydroxyl group and further an aromatic ring such as 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, glycerol mono(meth)acrylate, diethylene glycol mono(meth)acrylate, triethylene glycol mono(meth)acrylate, pentaethylene glycol mono(meth) acrylate, polyethylene glycol mono (meth)acrylate, dipropylene glycol mono (meth)acrylate, 2-hydroxy-3-phenoxypropyl (meth)acrylate, (HPPM in the case of methacrylate), 2-hydroxy-3-naphthoxypropyl (meth)acrylate (HNPM in the case of methacrylate), addition reaction product of GMA and an aliphatic or aromatic polyol (including phenol) such as an addition reaction product (Bis-GMA in case of methacrylate) of 1 mole of bisphenol A and 2 moles of glycidyl (meth)acrylate (GMA in the case of methacrylate); (meth)acrylamides containing a hydroxyl group such as methylol (meth)acrylamide, N-(meth)acryloyl-2,3-dihydroxypropylamine and N-(meth)acryloyl-1,3-dihydroxypropylamine; hydroxyalkyl (meth)acrylates having a halogen such as chlorine, such as 3-chloro-2-hydroxypropyl (meth)acrylate; and polyethylene glycol mono(meth)acrylates having a methyl or ethyl substituent such as ethylene glycol mono(meth)acrylate, diethylene glycol mono(meth)acrylate, triethylene glycol mono (meth)acrylate, polyethylene glycol mono (meth)acrylate, methoxydiethylene glycol mono (meth)acrylate, methoxytetraethylene glycol (meth)acrylate and methoxypolyethylene glycol (meth)acrylate.

The above monofunctional polymerizable monomers may be used alone or in combination of two or more.

Since the monofunctional polymerizable monomer has a lower polymerization rate than that of the polyfunctional polymerizable monomer, it can extend the curing time when a curable composition is to be formed. Therefore, the working time can be prolonged.

[Polymerization Initiator (B)]

The component (B) is a polymerization initiator. The polymerization initiator is selected from a polymerization initiator, a curing agent and an accelerator all of which can be used for dental materials and surgical materials. At least one of them is preferably contained, or they may be used in combination according to use conditions. The polymerization initiator is preferably a polymerization initiator which can radically polymerize a polymerizable monomer, particularly preferably a boron-containing polymerization initiator. The polymerization initiator is preferably an organic boron compound or a composition containing the same. Examples of the organic boron compound include tri(cyclo)alkylborons such as triethylboron, tripropylboron, triisopropylboron, tributylboron, tri-sec-butylboron, triisobutylboron, tripentylboron, trihexylboron, trioctylboron, tridecylboron, tridodecylboron, tricyclopentylboron and tricyclohexylboron; alkoxyalkylborons such as butoxydibutylboron; and dialkylboranes and compounds obtained by partial oxidizing of the above compounds such as butyldicyclohexylborane, diisoamylborane and 9-borabicyclo[3.3.1]nonane.

Further, these compounds may be used in combination. Out of these, tributylboron or partially oxidized tributylboron is preferably used. The partially oxidized tributylboron is obtained by adding preferably 0.3 to 0.9 mole, more preferably 0.4 to 0.6 mole of oxygen to 1 mole of tributylboron.

A composition comprising an aprotic solvent and/or a liquid or solid organic oligomer or polymer which is inert to an organic boron compound in addition to the organic boron compound may be used.

Examples of the organic boron compound include the above alkylboron derivatives and arylboron derivatives. The arylboron derivatives include borate compounds having 1 to 4 boron-aryl bonds in one molecule. Borate compounds having 3 boron-aryl bonds include sodium salts, lithium salts, potassium salts, magnesium salts, tetrabutylammonium salts, tetramethylammonium salts, tetraethylammonium salts, tributylammonium salts, triethanolammonium salts, methylpyridinium salts, ethylpyridinium salts, butylpyridinium salts, methylquinolinium salts, ethylquinolinium salts or butylquinolinium salts of monoalkyl triphenylboron, monoalkyl tris(p-chlorophenyl)boron, monoalkyl tris(p-fluorophenyl)boron, monoalkyl tris(3,5-bistrifluoromethyl)phenylboron, monoalkyl tris[3,5-bis(1,1,1,3,3,3-hexafluoro-2-methoxy-2-propyl)phenyl]boron, monoalkyl tris(p-nitrophenyl)boron, monoalkyl tris(m-nitrophenyl)boron, monoalkyl tris(p-butylphenyl)boron, monoalkyl tris(m-butylphenyl)boron, monoalkyl tris(p-butyloxyphenyl)boron, monoalkyl tris(m-butyloxyphenyl)boron, monoalkyl tris(p-octyloxyphenyl)boron and monoalkyl tris(m-octyloxyphenyl)boron (in these compounds, the alkyl is n-butyl, n-octyl or n-dodecyl).

Borate compounds having 4 boron-aryl bonds in one molecule include sodium salts, lithium salts, potassium salts, magnesium salts, tetrabutylammonium salts, tetramethylammonium salts, tetraethylammonium salts, tributylammonium salts, triethanolammonium salts, methylpyridinium salts, ethylpyridinium salts, butylpyridinium salts, methylquinolinium salts, ethylquinolinium salts or butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyoxyphenyl)boron and tetrakis(m-octyloxyphenyl)boron (in these compounds, the alkyl is n-butyl, n-octyl or n-dodecyl).

These arylboron derivatives also include compounds enumerated in JP-A 2002-187907 and JP-A 2003-96122.

[X-Ray Impermeable Filler (C)]

The component (C) is an X-ray impermeable filler. The X-ray impermeable filler is, for example, an X-ray impermeable filler which has been used for dentistry. Preferred materials for the above filler include substances having a heavy atom such as zirconium, zinc, barium, bismuth and tungsten, as exemplified by zirconium oxide, zinc oxide, barium sulfate, bismuth oxide, bismuth oxychloride, bismuth oxide carbonate, calcium tungstate and mixtures thereof. These fillers may be used alone or in combination of two or more. The filler may be surface treated with a surface treating agent such as a silane compound or a titanium compound, coated with a polymer or buried in a polymer.

When the atomic weight of the heavy atom is light or the content of the heavy atom in the filler is low, X-ray impermeability may lower. Therefore, the X-ray impermeability of the filler is preferably not less than 200% Al, more preferably not less than 300% Al, much more preferably not less than 400% Al when measured in accordance with ISO6876 (dental root canal filling material).

Two or more fillers which differ in particle diameter may be used in combination. For example, a filler having a particle diameter of 0.001 to 1 μm and a filler having a particle diameter of 2 to 50 μm may be used in combination. Viscosity or flowability suitable for root canal filling work can be provided by combining these fillers when a curable composition for filling a dental root canal is to be prepared.

A filler except for the X-ray impermeable filler may be optionally contained in the composition of the present invention for the propose of viscosity or flowability.

[Soft Resin Material (D1)]

The component (D1) contained in the present invention is a soft resin material. The soft resin material preferably has a durometer A hardness of not more than 90 or a durometer D hardness of not more than 60. More preferably, the durometer A hardness is not more than 70 or the durometer D hardness is not more than 50. Much more preferably, the durometer A hardness is not more than 60 or the durometer D hardness is not more than 30. When the durometer A hardness is more than 90 or the durometer D hardness is more than 60, it may be difficult to remove a cured product of the curable composition for filling a dental root canal at the time of re-treating a root canal disadvantageously. There are three types of durometers based on JIS K6253 which are a middle hardness durometer (type A durometer), a high hardness durometer (type D durometer) and a low hardness durometer (type E durometer). Numerical values obtained by these different types of hardness meters are expressed as durometer A hardness, durometer D hardness and durometer E hardness, respectively. In general, when the hardness value measured with a type A durometer based on JIS K6253 is less than 20, it is recommended to measure with a type E durometer and when the hardness value is more than 90, it is recommended to measure with a type D durometer.

Therefore, it is preferred that at least the durometer A hardness should satisfy the above upper limit value. Although the lower limit is not particularly limited, when the above recommendation (when the durometer A hardness is less than 20, a durometer E hardness parameter is employed) is taken into consideration, the durometer E hardness should be used according to circumstances. Preferably, the durometer A hardness is not less than 20 or the durometer E hardness is not less than 1, more preferably not less than 5, much more preferably not less than 10. Below the above lower limit, when the soft resin material is a pellet and not a powder, grinding work for reducing the particle diameter to a desired value becomes difficult disadvantageously. The soft resin material is preferably a powder and its particle diameter is not particularly limited as long as it is powdery. When the dispersibility into the component $(A_1)$ and filling property of the soft resin material are taken into consideration, the particle diameter is preferably 0.001 to 2,000 μm, more preferably 0.01 to 1,000 μm, much more preferably 0.1 to 500 μm. When the composition is applied to a tooth, if the soft resin material is existent in the domain of the above size in a cured product, the removal of the cured product becomes easy advantageously. That is, the soft resin material (D1) is preferably a resin which is not substantially dissolved by the component (A) or $(A_1)$, more preferably a resin which has low compatibility with the components (A) or $(A_1)$ and (E), polymers thereof and the component (D2) which will be described hereinafter.

The soft resin material can be selected from so-called soft resins and can be obtained by selecting the type of molecule constituting the resin and adjusting the molecular weight and distribution of the molecular weight, the ratio of comonomers, and the type and amount of a material to be mixed. Examples of the soft resin material include gutta-percha, polyethylene, polypropylene, ethylene propylene copolymer, ethylene propylene terpolymer, polyisoprene, ethylene vinyl acetate copolymer, silicone polymer, and ethylene-(meth) acrylate copolymers such as ethylene-methyl (meth)acrylate copolymer, ethylene-ethyl (meth)acrylate copolymer and ethylene-butyl (meth)acrylate copolymer. They may be used alone or in combination of two or more. Gutta-percha is generally natural rubber and comprises trans-polyisoprene as the main ingredient. Cis-polyisoprene and trans-polyisoprene and atactic polyisoprene which is a mixture thereof may be used as synthetic polyisoprene. Out of these, trans-polyisoprene is preferably used.

The composition of the first dental curable composition of the present invention is a dental composition which comprises (A) a polymerizable monomer and (B) a polymerization initiator as essential ingredients, wherein the above component (A) contains (A') a long-chain polymerizable monomer having a structure with a chain length of 17 or more atoms and/or the composition contains (D1) a soft resin material; and when the amount of the component (A') based on 100 parts by weight of the component (A) is represented by [a'] and the amounts of the components (A), (B) and (D1) based on 100 parts by weight of the total of the component (A) which may contain the component (A') and the component (B) are represented by (A), (b) and (d1), respectively, the following expression are satisfied:

$$70 \leq (A) \leq 99.99$$

$$0.01 \leq (b) \leq 30$$

$$1 \leq [a']/5 + (d1)/1$$

$$[a'] \leq 95$$

$$(d1) \leq 250.$$

More preferably, the amount of the component (A) is 80 to 99.9 parts by weight, and the amount of the component (B) is 0.05 to 20 parts by weight. Much more preferably, the amount of the component (A) is 90 to 99.5 parts by weight, the amount of the component (B) is 0.1 to 10 parts by weight, and the total of the components (A) and (B) is 100 parts by weight.

When the amount of the component (A) falls below the lower limit or the amount of the component (B) exceeds the upper limit, polymerization becomes too fast. When the amount of the component (A) exceeds the upper limit or the amount of the component (B) falls below the lower limit, polymerization becomes incomplete disadvantageously.

When the amount of the component (A') contained in the component (A) based on 100 parts by weight of the component (A) is represented by [a'] and the amount of the component (D1) based on 100 parts by weight of the total of the component (A) which may contain the component (A') and the component (B) is represented by (d1), the following expressions are satisfied:

$$1 \leq [a']/5 + (d1)/1,$$

$$[a'] \leq 95, \text{ and}$$

$$(d1) \leq 250.$$

A detailed description is given of the relational expression between the above component (A') and the component (D1).

As for the definition of [a'], since the component (A') is lower conception than the component (A), $$[a'] = W_{(A')}/W_{(A)} = W_{(A')}/(W_{(A')} + W^-_{(A')})$$

($W_{(A')}$ is the weight of the component (A'), $W_{(A)}$ is the weight of the component (A), and $W^-_{(A')}$ is the weight of the component (A) excluding the component (A').)

The critical significances of the lower limit values of the component (A') and the component (D1) are connected with an easy removal effect, and their functions and mechanism work independently. In other words, they have a mathematically linear connection relationship. Therefore, when each of them is used alone and their amounts fall below the lower limit values, there is a case in which the effect of the present invention can be obtained as they compensate for each other.

The conditions for the lower limit values when they are used alone are defined as follows.

$A'_L \leq A'_i$ ($A'_i$: the amount of the component (A'), $A'_L$: lower limit of the amount of the component (A'))

$D1_L \leq D1_i$ ($D1_i$: the amount of the component (D1), $D1_L$: lower limit of the amount of the component (D1))

Since these components differ from each other in lower limit value, the both sides are divided by the respective lower limit values to be normalized.

$$1 \leq A'_i/A'_L$$

$$1 \leq D1_i/D1_L$$

That is, if any one of them exceeds 1, the effect of the present invention is obtained. However, even if both of them are smaller than 1, when the total of them is 1 or more, it can be considered that the effect of the present invention is obtained. Therefore, when the both components are coexistent, if the following condition is satisfied, the effect of the present invention must be guaranteed.

$$1 \leq A'_i/A'_L + D1_i/D1_L$$

It is needless say that the above relational expression shows the lower limit value when the amount of one component is 0 and the other component is used alone. Therefore, as for the lower limits of the amounts of the components (A') and (D1) alone, the lower limit of the amount of the component (A') is 5 parts by weight (based on 100 parts by weight of the component (A) containing the component (A')) and the lower limit of the amount of the component (D1) is 1 part by weight (based on 100 parts by weight of the total of the components (A) and (B)). Therefore, by inserting these values into $A'_L$ and $D1_L$, respectively, the above relational expression is obtained.

The lower limit of the amount of the component (A') when it is used alone is preferably 10 parts by weight, more preferably 15 parts by weight, and the lower limit of the amount of the component (D1) when it is used alone is preferably 30 parts by weight, more preferably 50 parts by weight. It is needless to say that a more preferred relational expression is obtained by inserting these into $A'_L$ and $D1_L$, respectively. As for the upper limit values, when the amount of the component (A') contained in the component (A) based on 100 parts by weight of the component (A) is represented by [a'] and the amount of the component (D1) based on 100 parts by weight of total of the component (A) including the component (A') and the component (B) is represented (d1), [a']≦95, preferably [a']≦80, more preferably [a']≦65, and (d1)≦250, preferably (d1)≦200, more preferably (d1)≦150.

When the amount of the component (A') exceeds the above upper limit value, the amount of the polymerizable monomer having an acid group becomes small inevitably with the result that marginal sealability is reduced due to the insufficient decalcification of the tooth disadvantageously. When the amount of the component (D1) exceeds the above upper limit value, the amount of the polymerizable monomer which can permeate the tooth becomes small, whereby a high-quality layer structure in which different components are intertwined with one another 3-dimensionally is not formed, thereby reducing marginal sealability. Since the non-preferable reasons why the amounts of the above components exceed the upper limit values differ from each other, they are independent without interfering with each other.

Based on 100 parts by weight of the amount of the component (A), the amount of the polymerizable monomer having an acid group contained in the component (A) is preferably 0.1 to 40 parts by weight, more preferably 1 to 30 parts by weight, much more preferably 3 to 25 parts by weight. Below the above lower limit, the effect of promoting the permeability into the tooth of the component (A) having no acid group is reduced and the tooth is decalcified insufficiently and above the upper limit, the tooth is decalcified excessively disadvantageously.

When the component (A') has a relatively short chain length of 34 or less atoms or 9 or less ethylene glycol units, a large amount of the component (A') is required to achieve an easy removal effect. That is, the amount of the component (A') is preferably 10 to 97 parts by weight, more preferably 25 to 80 parts by weight, much more preferably 35 to 60 parts by weight.

Based on 100 parts by weight of the component (A), the amount of the polyfunctional polymerizable monomer contained in the component (A) is preferably 0.2 to 100 parts by weight, more preferably 10 to 70 parts by weight, much more preferably 25 to 60 parts by weight. The amount of the polyfunctional component excluding the component (A') is preferably 0.2 to 80 parts by weight, more preferably 0.7 to 30 parts by weight, much more preferably 1.5 to 10 parts by weight. Below the above lower limit, polymerization becomes incomplete and above the upper limit, removal becomes difficult disadvantageously. The amount of the polyfunctional component (A') is preferably 0 to 80 parts by weight, more preferably 10 to 70 parts by weight, much more preferably 25 to 65 parts by weight. Below the lower limit, easy removability degrades disadvantageously.

The dental curable composition may comprise a component (X) which does not belong to all of the above components (A) to (D1), and the amount of the above component (X) is preferably not more than 400 parts by weight based on 100 parts by weight of the total of the components (A) to (D1) which are added without being overlapped. Examples of the component (X) include the following components (D2) to (H). When the component (X) is a component which is compatible with a mixture of the components (A) to (D1), the amount of the component (X) is preferably not more than 100 parts by weight.

[Polymer (D2) Excluding the Component (D1), Which is Swollen or Dissolved by the Component (A) or ($A_1$)]

The component (D2) which is optionally used in the present invention is a polymer excluding the component (D1), which is swollen or dissolved by the component (A) or ($A_1$) and is not limited to specific hardness. Its durometer D hardness is preferably not less than 40, more preferably not less than 50, much more preferably not less than 60.

The component (D2) is powdery with an average particle diameter of preferably 1 to 300 μm, more preferably 10 to 100 μm. Below the lower limit or above the upper limit, the manipulation ease of the composition may be lost disadvantageously. The component (D2) is a polymer which is swollen or dissolved by the component (A) or ($A_1$) to increase the viscosity of a liquid containing the component (A) or ($A_1$) and adjust the curing time. It is, for example, a homopolymer or copolymer of a monofunctional polymerizable monomer used as the component (A) or ($A_1$). Specific examples of the component (D2) include polymethyl (meth)acrylate, polyethyl (meth)acrylate, polypropyl (meth)acrylate, polybutyl (meth)acrylate, and copolymers of methyl (meth)acrylate and ethyl (meth)acrylate.

[Polyfunctional Polymerizable Monomer (E)]

The component (E) is a polyfunctional polymerizable monomer. The component (E) is optionally used. The component (E) is mainly used to adjust the curing speed of the curable composition and increase the mechanical strength of a cured product.

Specific examples of the bifunctional polymerizable monomer include aliphatic esters of (meth)acrylic acid such as methylene glycol di(meth)acrylate, neopentyl glycol di(meth)acrylate and 1,3-butylene glycol di(meth)acrylate;

aromatic (meth)acrylates such as an adduct of 1 mole of bisphenol A with 2 moles of glycidyl (meth)acrylate; polyethylene glycol di(meth)acrylates such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate; polypropylene glycol di(meth)acylates such as propylene glycol di(meth)acrylate, dipropylene glycol di(meth)acrylate, tripropylene glycol di(meth)acrylate and nonapropylene glycol di(meth)acrylate; (meth)acrylates having a urethane bond such as an adduct of 2-(meth)acryloyloxyethyl isocyanate, 2,2,4-trimethylhexamethylene diisocyanate or 1,3,5-trimethylhexamethylene diisocyanate with 2-hydroxyethyl (meth)acrylate; and 2,2-bis(4-(meth)acryloyloxypolyethoxyphenyl)propanes obtained by condensing (meth)acrylic acid to a product obtained by adding bisphenol A to oxyethylene.

(iii) Examples of the polyfunctional polymerizable monomer having 3 or more polymerizable groups include trifunctional polymerizable monomers such as trimethylolalkane tri(meth)acrylates including trimethylolmethane tri(meth)acrylate ($CH_3-CH_2-C(-CH_2O-CO-CR=CH_2)_3$, R:H or $CH_3$), trimethylolethane tri(meth)acrylate and trimethylolpropane tri(meth)acrylate, and (meth)acrylate esters of tris (2-hydroxyethyl)isocyanurate; tetrafunctional polymerizable monomers such as tetra(meth)acrylates of polymethylolalkanes or ethers thereof including pentaerythritol tetra(meth)acrylate and ditrimethylolpropane tetra(meth)acrylate ($O(-CH_2-C(-CH_2O-CO-CR=CH_2)_2CH_2CH_3)_2$, R:H or $CH_3$); and penta- or more functional polymerizable monomers such as poly(meth)acrylates of polymethylolalkanes or ethers thereof including dipentaerythritol hexa (meth)acrylate and dipentaerythritol hydroxypenta(meth)acrylate.

The polymerizable monomers having two or more polymerizable groups also include compounds having a methacrylate group and an acrylate group in one molecule such as triethylene glycol acrylate methacrylate, trimethylolpropane monoacrylate dimethacrylate and pentaerythritol diacrylate dimethacrylate.

The above polyfunctional polymerizable monomers (E) may be used alone or in combination of two or more.

[Disinfecting Agent (F)]

The component (F) is a disinfecting agent. The component (F) is optionally used. The component (F) is used to enhance disinfection when it is used after the treatment of an infected root canal and is not particularly limited as long as it can disinfect or eliminate bacteria. Specific examples of the component (F) include benzalkonium chloride, benzethonium chloride, isopropyl methyl phenol, cetyl pyridinium chloride, resorcin, chlorhexidine hydrochlorate, chlorhexidine gluconate, iodine, potassium iodide, povidone-iodine and iodoform. At least one of them is preferably contained to enhance disinfection.

The dental curable composition according to a fourth embodiment of the present invention comprises the above components (A), (B) and (D1) and optionally the components (E), (F) and a solvent (G). The solvent (G) used herein is preferably a solvent having compatibility with the long-chain polymerizable monomer (A'). The expression "having compatibility" means, but not particularly limited, that not less than 3 parts by weight of the long-chain polymerizable monomer (A') can be dissolved uniformly in 100 parts by weight of the solvent. However, since there is no problem if a homogeneous composition is obtained in the end, a homogeneous solution should be obtained by mixing together all the components even if the solvent and each of other individual components cannot form a homogeneous solution. For example, a polymerizable monomer having appropriate compatibility (such as 2-hydroxyethyl (meth)acrylate) is used.

Particularly when the long-chain polymerizable monomer (A') has an oxyalkylene structure, especially an ethylene glycol recurring unit, an aqueous solvent is preferably used, and water alone or a mixture of water and an organic solvent which can be mixed with water is used as a solvent. Examples of water which can be used herein include distilled water and ion exchange water. Physiological saline may also be used as the aqueous solvent. Out of these, distilled water and ion exchange water are preferably used. Examples of the organic solvent which can be mixed with the above water include alcohols such as methanol, ethanol and propanol, ketones such as acetone and methyl ethyl ketone, ethers such as tetrahydrofuran, amides such as N,N-dimethylformamide, and aprotic solvents such as dimethyl sulfoxide. When damage and irritation to the dental pulp are taken into consideration, ethanol and acetone out of these organic solvents are preferably used.

The dental curable composition according to a fifth embodiment of the present invention comprises preferably 0.1 to 100 parts by weight, more preferably 0.3 to 50 parts by weight, much more preferably 0.5 to 25 parts by weight of the component (G) based on 100 parts by weight of the total of the components (A), (B) and (D1). It should be understood that the relative ratio of the components (A), (B), (D1) and (G) in the composition should be the same as in the first, second, third and fourth dental curable compositions. When the content of the component (G) is high, a primer effect tends to become strong and in this case, it can be actually used as a primer.

[Filler (H)]

The component (H) is a filler. The component (H) is optionally used. The component (H) is an inorganic filler or an organic composite filler and mainly used to adjust viscosity. Besides amorphous silica and quartz, an inorganic filler which comprises not less than 50% of silicon dioxide as a constituent component and at least one oxide of a metal such as barium, strontium, aluminum, zinc, bismuth, zirconium or lanthanum as the other constituent component may also be used as the inorganic filler. The inorganic filler may be surface treated with a silane coupling agent or a titanate coupling agent in advance. The organic composite filler refers to a filler obtained by polymerizing a polymerizable monomer to cover the surface of an inorganic oxide such as particulate silica therewith and grinding the obtained product. A TMPT filler obtained by polymerizing a polymerizable monomer comprising trimethylolpropane tri(meth)acrylate (TMPT) as the main ingredient to cover the surface of an inorganic oxide therewith and grinding the obtained product is such an example.

The particle diameter of the filler is not particularly limited but preferably 0.005 to 50 μm, more preferably 0.005 to 10 μm. These fillers may be used alone or in combination. The particles of the filler are not limited to a particular shape and may be amorphous, spherical or needle-like and may be in a porous form or core-shell form.

[Easily Removable Dental Curable Composition]

As for the amount of each component, the amount of the component ($A_1$) is 1 to 70 parts by weight, preferably 5 to 60 parts by weight, more preferably 10 to 50 parts by weight, much more preferably 20 to 48 parts by weight based on 100 parts by weight of the total of the components ($A_1$), (B), (c) and (D1). Below the above lower limit, flowability is lost and the resulting composition tends not to be applicable to a thin root canal and above the upper limit, contrast properties tend to deteriorate disadvantageously.

The amount of the component (B) is 0.1 to 20 parts by weight, preferably 0.5 to 15 parts by weight, more preferably 0.7 to 10 parts by weight, much more preferably 1 to 5 parts by weight based on the same standard. Below the above lower limit, the curing time tends to become too long and above the upper limit, the curing time tends to become too short disadvantageously.

The amount of the component (C) is 1 to 80 parts by weight, preferably 5 to 70 parts by weight, more preferably 10 to 65 parts by weight, much more preferably 15 to 60 parts by weight based on the same standard. Below the above lower limit, contrast properties tend to become unsatisfactory and above the upper limit, flowability tends to be lost disadvantageously.

The amount of the component (D1) is 0.1 to 60 parts by weight, preferably 1 to 55 parts by weight, more preferably 5 to 50 parts by weight, much more preferably 5 to 40 parts by weight based on the same standard. Below the above lower limit, the effect of the soft resin material on the mechanical properties of a cured product tends not to be observed and above the upper limit, a cured product tends to become too brittle disadvantageously.

When the component (D2) is further contained, the amount of the component (D2) is preferably 0.1 to 60 parts by weight, more preferably 1 to 40 parts by weight, much more preferably 3 to 30 parts by weight, particularly preferably 5 to 15 parts by weight based on the same standard. Below the above lower limit, the effect of adjusting the curing time is hardly observed and above the upper limit, curing becomes very fast or viscosity becomes high, thereby making it difficult to handle the composition disadvantageously.

The polyfunctional polymerizable monomer (E) is contained in an amount of 0.05 to 20 parts by weight based on the same standard. When the amount of the component (E) falls within the above range, the operation time can be set long and the curing time can be set short. It is more preferably 0.1 to 15 parts by weight, much more preferably 0.5 to 10 parts by weight.

When the disinfecting agent (F) is further contained, the amount of the component (F) is preferably 0.01 to 20 parts by weight based on the same standard. When the amount of the component (F) falls within the above range, bactericidal or disinfectant curing can be developed right after filling. It is more preferably 0.05 to 10 parts by weight, much more preferably 0.1 to 5 parts by weight.

When the filler (H) is further contained, the amount of the component (H) is preferably 0.01 to 30 parts by weight based on the same standard. It is more preferably 0.1 to 20 parts by weight, much more preferably 1 to 10 parts by weight. Below the above lower limit, the effect of adjusting viscosity is hardly observed and above the upper limit, viscosity becomes too high, thereby making it difficult to handle the composition disadvantageously.

Before the use of the curable composition of the present invention, it may be brought into direct contact with the tooth. According to circumstances, the inside of a root canal may be cleaned with a liquid containing a hydrogen peroxide solution or a sodium hypochloride aqueous solution. Before the application of the curable composition, the surface of the tooth is preferably pre-treated with an etching agent and/or a tooth surface treating agent such as a primer. Examples of the etching agent include decalcifying compounds such as aqueous compositions having a pH of 5 or less and containing hydrochloric acid, nitric acid, sulfuric acid, phosphoric acid, citric acid or oxalic acid, ethylenediamine tetra-acetic acid or salt thereof (EDTA) having a pH of 9 or less disclosed by JP-A 61-183203 and Japanese Patent No. 2648163, and compounds having an aliphatic and/or aromatic amine such as diethylenetriamine or salt thereof (DTPA) and an acidic functional group such as acetic acid in the molecule as disclosed by JP-A 1-230510. These etching agent compositions preferably contain a metal ion such as calcium ion, ferric ion, copper ion or cobalt ion. An example of the primer is a composition comprising water and/or an organic solvent which can be mixed with water and the above component ($A_1$) and/or the component (B) in the present invention.

Examples of the organic solvent which can be mixed with water include alcohols such as methanol, ethanol, propanol and isopropyl alcohol, ketones such as acetone and methyl ethyl ketone, ethers such as tetrahydrofuran (THF), amides such as N,N-dimethylformamide, and dimethyl sulfoxide (DMSO). Out of these, ethanol, acetone and DMSO are preferably used. The organic solvent which can be used herein plays an important role as a carrier for diffusing the curable composition components of the present invention into a bio tissue having a high water content.

Before the root canal filling curable composition is applied to the inside of a root canal, it may be cleaned by a commonly used method but it is preferred that the surface of a tooth should be etched with an aqueous solution containing citric acid and ferric chloride or an etching agent containing EDTA or DTPA, preferably a primer containing the component ($A_1$) and/or a metal ion. It is particularly preferred that the formation of resin impregnated tooth should be observed near contact between the curable composition and the root canal wall from the viewpoint of exhibiting and maintaining high sealability.

When the curable composition of the present invention is applied to the inside of a root canal, another generally known root canal filling material such as gutta-percha containing a thermoplastic resin composition having X-ray contrast properties may be used in combination.

As described above, the object of the present invention can be advantageously attained by combining the root canal filling curable composition and the tooth surface treating agent and/or the thermoplastic resin composition having X-ray contrast properties. According to the present invention, there is provided a dental kit which is a combination of the dental canal filling curable composition of the present invention and the tooth surface treating agent.

EXAMPLES

The following examples are provided for the purpose of further illustrating the present invention but are in no way to be taken as limiting.

<Micro-Tensile Bond Strength Test>

A root canal was expanded to form a cylindrical cavity having a diameter of 4 mm by using a bovine dental root which was unfrozen right before the test. Water in the enlarged root canal was removed by an air gun, the root canal was treated with an aqueous solution containing 10% of citric acid and 3% of ferric chloride (to be referred to as "10-3 solution" hereinafter) for 10 seconds and rinsed in water fully, and the inside of the root canal was dried with a paper point and filled with the composition of the present invention. After the root canal was left in a thermostat bath having a relative humidity of 95% and a temperature of 37° C. for 24 hours, it was cut in half on a plane passing through the center part of the cylindrical cavity filled with the composition in parallel to the root canal direction. 20 minutes after a 1000 $mm^3$ (10 mm×10 mm×10 mm) acrylic cube was bonded to the cut surface with Super Bond C&B (of Sun Medical Co., Ltd.), it was cut to a thickness of about 1 mm in a direction perpendicular to the root canal direction with the ISOMET low-speed rotary diamond cutter (of BUEHLER Co., Ltd.). Further, the obtained piece was trimmed to a dumbbell-like form (thinnest portion: interface between the tooth and the filled composition) to ensure that the bonding area became 1 mm$^2$, and then a micro-tensile bond strength test was carried out on the piece at a cross head speed of 1 mm/min with the EZ-TEST small-sized desk-top tester (of Shimadzu Corporation).

<Marginal Sealability Test/Removability Test>

A root canal was expanded to form a cylindrical cavity having a diameter of 4 mm by using a bovine dental root which was unfrozen right before the test. Water in the enlarged root canal was removed by an air gun, the root canal was treated with the 10-3 solution for 10 seconds and rinsed in water fully, and the inside of the root canal was dried with a paper point and filled with the composition of the present invention. After the root canal was left in a thermostat bath having a relative humidity of 95% and a temperature of 37° C. for 24 hours, it was cut to a thickness of 5 to 8 mm in a direction perpendicular to the root canal direction with the ISOMET low-speed rotary diamond cutter. Further, the obtained sample was immersed in a 5% methylene blue aqueous solution for 1 hour and cut in half on a plane passing through the center part of the cylindrical cavity filled with the composition in parallel to the root canal direction.

The filled composition was removed by using a barbed broach or resin remover to evaluate its removability as good when it could be easily removed. That is, when 4 or more out of 5 dental technicians having an experience of 2 years or more judge that the composition is easily removed, removability is evaluated as satisfactory, when 3 or 2 dental technicians judge that the composition is easily removed, removability is evaluated as acceptable, and when 1 or less dental technician judges that the composition is easily removed, removability is evaluated as unacceptable.

As for marginal sealability, the degree of entry of a pigment at the interface of tooth when the composition was removed was judged. As for judgment on marginal sealability, a numerical value obtained by dividing the area where the pigment enters by the total bonding area is rounded off to two decimal places and classified as follows.

⊚: 0, ○: ~0.20, Δ: 0.21 to 0.50, X: ≧0.51 (0 means that the entry of the pigment is not observed at all.)

<X-Ray Contrast Property Test>

This was carried out in accordance with ISO6876 (dental root canal filling material).

<Scanning Electron Microscope Observation/Elemental Analysis>

After a root canal was expanded with Engine Reamer (#45 of Mani, INC.) by using a removed single human dental root and cleaned with a solution containing 15% of ethylenediamine tetra-acetic acid (EDTA) and 2.5% of sodium hypochloride (NaClO). After it was rinsed in water, water was removed with a paper point, the composition was filled by a single point method using a gutta-percha point and kept in a 37° C. humid environment for one night. Thereafter, the sample was cut in the tooth axis direction under the injection of water, mirror polished and treated with 6 N hydrochloric acid and 1% NaClO to observe the bonded interface between the dentine of the root canal and a sealer and the bonded interface between the sealer and the gutta-percha point through a scanning electron microscope (SEM: JEOL Limited., JSM-5610LV). Elemental analysis was carried out on portions near these bonded interfaces with an energy diffusion type X-ray analyzer (EDS: JEOL Ltd., JED-2200).

Example 1

A liquid was prepared by dissolving 5 parts by weight of 4-methacryloxyethyl trimellitate anhydride (4-META) which is solid in 95 parts by weight of methyl methacrylate (MMA). Right after 0.09 g of this liquid and 0.006 g of tributylboron (TED, partial oxide of B(C$_4$H$_9$)$_3$ loaded with about 0.3 mole/mole oxygen) were mixed together, 0.075 g of zirconium oxide (particle diameter of 0.005 to 30 μm), 0.015 g of polymethyl methacrylate powders (number average molecular weight of 40,000, weight average molecular weight of 400,000, particle diameter of 36 μm, durometer D hardness of 66, to be referred to as "PMMA" hereinafter) and 0.02 g of ethylene vinyl acetate copolymer powders (Ultrasene; vinyl acetate content of 20%, average particle diameter of 62 μm, durometer A hardness of 85, to be referred to as EVA hereinafter) were added to the above mixture and mixed together at room temperature (24° C.). This slurry was used to carry out a micro-tensile test, a marginal sealability test, a removability test and an X-ray contrast property test. The results are shown in Table 1. Further, when the bonded interfaces were observed through a scanning electron microscope (SEM), it was confirmed that the bonded interfaces were in a well bonded state without a crack, a layer (resin impregnated layer) in which the composition infiltrated into the tooth and cured was observed, and further a layer in which the composition infiltrated into not only the tooth but also the gutta-percha point outermost layer and which was obviously different from the tooth portion and the point portion was observed. It was confirmed from the elemental analysis of these layers by EDS that both elements which were Ca derived from the tooth and C derived from the composition were seen at the interface between the tooth and the composition and that both elements which were C derived from the composition and Zn derived from gutta-percha point were seen at the interface between the composition and the gutta-percha point. Thereby, it was judged that these layers were formed by the permeation into the tooth portion and the gutta-percha point portion and polymerization of the composition. When the SEM observation of the bonded interfaces and the elemental analysis of the layers were carried out in Examples 2 to 4, the same results were obtained.

Example 2

Right after 0.09 g of the liquid prepared in Example 1 and 0.006 g of TBB were mixed together, 0.058 g of zirconium oxide, 0.012 g of PMMA powders and 0.04 g of EVA were added to the resulting mixture and mixed together at room temperature. This slurry was used to carry out the same tests as in Example 1. The results are shown in Table 1.

Example 3

A liquid was prepared by dissolving 5 parts by weight of 4-META which is solid in 91.5 parts by weight of MMA and 3.5 parts by weight of glycerin dimethacrylate (GDMA). Right after 0.09 g of this liquid and 0.006 g of TBB were mixed together, 0.075 g of zirconium oxide, 0.015 g of PMMA powders and 0.02 g of ethylene propylene terpolymer powders (Mitsui EPT; average particle diameter of 216 μm, durometer A hardness of 60, to be referred to as EPT hereinafter) were added to the resulting mixture and mixed together at room temperature. This slurry was used to carry out the same tests as in Example 1. The results are shown in Table 1.

Example 4

A liquid was prepared by dissolving 5 parts by weight of 4-META which is solid and 1 part by weight of iodoform in 94 parts by weight of MMA. Right after 0.09 g of this liquid and 0.006 g of TBB were mixed together, 0.075 g of zirconium oxide (particle diameter of 0.005 to 30 nm), 0.015 g of PMMA powders and 0.02 g of EVA were added to the resulting mixture and mixed together at room temperature (24° C.). This slurry was used to carry out the same tests as in Example 1. The results are shown in Table 1.

Example 5

A liquid was prepared by dissolving 50 parts by weight of tricosane ethylene glycol dimethacrylate (23 G) and 2.5 parts by weight of 4-META in 47.5 parts by weight of MMA. Right after 0.106 g of this liquid and 0.006 g of TBB were mixed together, 0.128 g of zirconium oxide and 0.032 g of EVA were added to the resulting mixture and mixed together at room temperature. This slurry was used to carry out the same tests as in Example 1. The results are shown in Table 1.

Example 6

A liquid was prepared by dissolving 50 parts by weight of tricosane ethylene glycol dimethacrylate (23 G) and 2.5 parts by weight of 4-META in 47.5 parts by weight of MMA. Right after 0.106 g of this liquid and 0.006 g of TBB were mixed together, 0.113 g of zirconium oxide, 0.030 g of EVA and 0.008 g of a TMPT filler (average particle diameter of 5 μm) were added to the resulting mixture and mixed together at room temperature. This slurry was used to carryout the same tests as in Example 1. The results are shown in Table 1.

Comparative Example 1

Right after 0.09 g of the liquid prepared in Example 1 and 0.006 g of TBB were mixed together, 0.09 g of zirconium oxide (particle diameter of 0.005 to 30 μm) and 0.02 g of PMMA powders were added to the resulting mixture and mixed together at room temperature (24° C.). This slurry was used to carry out the same tests as in Example 1. The results are shown in Table 1.

Example 7

Components shown in Table 1 were used to prepare slurry in the same manner as in Example 6 so as to carry out the same tests as in Example 1 using this slurry. The result are shown in Table 1.

TABLE 1

| | | Ex. 1 | Ex. 2 | Ex. 3 | Ex. 4 | Ex. 5 | Ex. 6 | C. Ex. 1 | Ex. 7 |
|---|---|---|---|---|---|---|---|---|---|
| (A) | ($A_1$) | MMA [44.8] 4-META [2.3] | MMA [44.1] 4-META [2.3] | MMA [43.8] 4-META [2.4] | MMA [44.5] 4-META [2.4] | MMA [18.5] 4-META [1.0] | MMA [18.5] 4-META [1.0] | MMA [46.0] 4-META [2.4] | MMA [16.1] |
| | (A') | | | | | 23G [19.5] | 23G [19.5] | | 23G [6.5] 14G [19.4] |
| (B) | | TBB [3.1] | TBB [3.1] | TBB [3.2] | TBB [3.2] | TBB [2.2] | TBB [2.2] | TBB [3.2] | TBB [3.4] |
| (C) | | $ZrO_2$ [39.3] | $ZrO_2$ [29.9] | $ZrO_2$ [39.4] | $ZrO_2$ [39.4] | $ZrO_2$ [47.0] | $ZrO_2$ [47.0] | $ZrO_2$ [48.4] | $ZrO_2$ [43.1] |
| (D1) | | EVA [10.5] | EVA [20.6] | EPT [10.7] | EVA [10.5] | EVA [11.8] | EVA [11.8] | — | EVA [11.5] |
| (D2) | | PMMA [7.9] | PMMA [6.2] | PMMA [8.0] | PMMA [7.9] | — | — | PMMA [10.8] | — |
| (E) | | — | — | GDMA [1.7] | — | | | — | |
| (F) | | — | — | — | $CHI_3$ [0.5] | — | — | — | — |
| (G) | | — | — | — | — | — | — | — | $H_2O$ [9.8] |
| (H) | | — | — | — | — | — | TMPT Filler [2.9] | — | — |
| Micro-tensile bond strength (MPa) | | 20 | 16 | 21 | 18 | 13 | 14 | 28 | 11 |
| Marginal sealability | | ◎ | ○ | ◎ | Δ | ◎ | ◎ | ◎ | Δ |
| Removability | | satisfactory | satisfactory | satisfactory | satisfactory | satisfactory | satisfactory | not acceptable | satisfactory |
| X-ray contrast properties (% Al) | | 342 | 300 | 327 | 378 | 423 | 401 | 470 | 351 |

Ex.: Example C. Ex.: Comparative Example
The figures within the parentheses indicate parts by weight.

As shown in Table 1, the dental curable composition of the present invention has excellent adhesion to the dentine and marginal sealability and is excellent in X-ray contrast properties and removability. It is especially useful as a dental root canal filling curable composition and can greatly contribute to dentistry.

EFFECT OF THE INVENTION

The present invention can provide an easily removable dental curable composition which is an easily removable temporary prosthetic appliance and root canal filling material and is excellent in not only dentine adhesion, dentine bonding property, sealability and X-ray contrast properties but also the removability of the cured composition. Thereby, even when retreatment of root canal is needed, the cured composition can be easily removed, thereby making it possible to carry out the treatment of a dental root canal more safely and efficiently. Also, there is provided a dental curable composition which is very useful as a dental cervical caries repair resin material by providing flexibility and abrasion resistance when it comprises (A') a long-chain polymerizable monomer having a structure with a chain length of 17 or more atoms and/or (D1) a soft resin component. Further, a root canal filling composition which can exhibit performance expected for various states of the dental root wall stably can be provided by providing a root canal cleaner suitable for the root canal filling curable composition of the present invention.

The invention claimed is:

1. A dental curable composition which comprises (A) a polymerizable monomer mixture comprising a polymerizable monomer having acid group(s) in the molecule and (B) a polymerization initiator, wherein
   the composition comprises component (D1) and wherein component (A) optionally comprises component (A');
   wherein the component (A') is a long-chain polymerizable monomer having a structure with is length of 17 or more atoms and the component (D1) is a soft resin powder material which is not substantially dissolved and swollen by the above component (A) or (A');
   wherein the soft resin powder material (D1) is at least one selected from the group consisting of polyethylene, polypropylene, ethylene propylene copolymer, ethylene propylene terpolymer, ethylene vinyl acetate copolymer, silicone polymer and ethylene-(meth)acrylate copolymer; and
   when the amount of the component (A') based on 100 parts by weight of the component (A) is represented by [a'] and the amounts of the components (A), (B) and (D1) based on 100 parts by weight of the total of the components (A) and (B) are represented by (a), (b) and ($d_1$), respectively, the following expressions (1) to (5) are satisfied;

$70 \leq (a) \leq 99.99$ (1)

$0.01 \leq (b) \leq 30$ (2)

$1 \leq [a']/5 + (d_1)$ (3)

$[a'] \leq 95$ (4)

$(d1) \leq 250$ (5).

2. The dental curable composition according to claim 1, wherein the polymerizable monomer has at least one acid group selected from the group consisting of carboxylic acid group, phosphoric acid group, thiophosphoric acid group, sulfonic acid group, pyrophosphoric acid group and sulfinic acid group.

3. The dental curable composition according to claim 1, wherein the polymerizable monomer mixture (A) comprises a polymerizable monomer having at least one hydroxyl group in the molecule.

4. The dental curable composition according to claim 1, wherein the polymerizable monomer mixture (A) further comprises a polymerizable polyfunctional (meth)acrylate having 3 or more ethylenically unsaturated bonds.

5. The dental curable composition according to claim 1 wherein the polymerizable monomer mixture (A) further comprises a triazine ring derivative and/or a dipentaerythritol-based polymerizable monomer.

6. The dental curable composition according to claim 1, wherein the long-chain polymerizable monomer (A') has at least two polymerizable groups.

7. The dental curable composition according to claim 1, wherein the long-chain polymerizable monomer (A') is a polyalkylene glycol di(meth)acrylate having 4 or more oxyalkylene recurring units ($-(-(-CH_2-)_p-O-)_n-$; p is 2 or more, n is 4 or more).

8. The dental curable composition according to claim 1, wherein the long-chain polymerizable monomer (A') is polyethylene glycol di(meth)acrylate and/or polypropylene glycol di(meth)acrylate having 4 to 30 recurring units derived from propylene glycol and/or ethylene glycol.

9. The curable composition accord claim 1 which further comprises (C) an X-ray impermeable tiller.

10. The dental curable composition according to claim 1 which further comprises (G) a solvent having compatibility with the long-chain polymerizable monomer (A').

11. The dental curable composition according to claim 10, wherein the solvent (G) is an aqueous solvent.

12. The dental curable composition according to claim 10, wherein the solvent (G) is contained in an amount of 0.1 to 100 parts by weight based on 100 parts by weight of the total of the components (A), (B), (C) and (D1).

13. A dental curable composition comprising ($A_1$) a monofunctional polymerizable monomer mixture containing 0.1 to 30 wt % of a monofunctional polymerizable monomer having acid group(s) in the molecule and 99.9 to 70 wt % of a monofunctional polymerizable monomer haying no acid group in the molecule, (B) a polymerization initiator, (C) an X-ray impermeable filler and (D1) a soft resin powder material which is not substantially dissolved and swollen by the above component ($A_1$),
   wherein the soft resin powder material (D1) is at least one selected from the group consisting of polyethylene, polypropylene, ethylene propylene copolymer, ethylene propylene terpolymer, ethylene vinyl acetate copolymer, silicone polymer and ethylene-(meth)acrylate copolymer; and wherein
   the amount of the component ($A_1$) is 1 to 70 parts by weight, the amount of the component (B) is 0.1 to 20 parts by weight, the amount of the component (C) is 1 to 80 parts by weight and the amount of the component (D1) is 0.1 to 60 parts by weight based on 100 parts by of the total of the components ($A_1$), (B), (C) and (D1).

14. The curable composition according to claim 1, wherein the soft resin powder material (D1) is at least one selected from the group consisting of polyethylene, polypropylene, ethylene propylene copolymer, ethylene propylene terpolymer, ethylene vinyl acetate copolymer, silicone polymer and ethylene-(meth)acrylate copolymer.

15. The curable composition according to claim 1, wherein the soft resin powder material (D1) has a durometer A hardness of not more than 90 or a durometer D hardness of not more than 60.

16. The curable composition according to claim 1 which further comprises (D2) a polymer other than the component (D1), wherein the polymer (D2) is swollen or dissolved by the component (A) or ($A_1$).

17. The curable composition according to claim 16, wherein the component (D2) is contained in an amount of 0.1 to 60 parts by weight based on 100 parts by weight of the total of the component (A) or ($A_1$), the component (B), the component (C) and the component (D1) (the total amount of the component (C) and/or the component (D1) can be 0).

18. The curable composition according to claim 1 which further comprises (E) a polyfunctional polymerizable monomer.

19. The curable composition according to claim 18, wherein the component (E) is contained in an amount of 0.05 to 20 parts by weight based on 100 parts by weight of the total of the component (A) or ($A_1$), the component (B), the component (C) and the component (D1).

20. The curable composition according to claim 9, wherein the X-ray impermeable filler (C) is at least one selected from the group consisting of zirconium oxide, zinc oxide, barium sulfate, bismuth oxide, bismuth oxychloride, bismuth oxide carbonate and calcium tungstate.

21. The curable composition according to claim 1 which further comprises (F) a disinfecting agent.

22. The curable composition according to claim 21, wherein the disinfecting agent (F) contains at least one selected from the group consisting of benzalkonium chloride, benzethonium chloride, isopropyl methyl phenol, cetyl pyridinium chloride, resorcin, chlorhexidine hydrochloride, chlorhexidine gluconate, iodine, potassium iodide, povidone-iodine and iodoform.

23. The curable composition according to claim 22, wherein the component (F) is contained in an amount of 0.01 to 20 parts by weight based on 100 parts by weight of the total of the component (A) or ($A_1$), the component (B), the component (C) and the component (D1).

24. A dental kit which is a combination of the dental root canal filling curable composition of claim 13 and a dentine surface treating agent.

\* \* \* \* \*